US 8,439,681 B2

(12) United States Patent
Mandelis et al.

(10) Patent No.: US 8,439,681 B2
(45) Date of Patent: May 14, 2013

(54) METHOD OF ASSESSING ORAL HEALTH RISK

(75) Inventors: Andreas Mandelis, Scarborough (CA); Stephen Abrams, Toronto (CA)

(73) Assignee: Quantum Dental Technologies, Toronto, ON (CA)

( * ) Notice: Subject to any disclaimer, the term of this patent is extended or adjusted under 35 U.S.C. 154(b) by 241 days.

(21) Appl. No.: 12/718,746

(22) Filed: Mar. 5, 2010

(65) Prior Publication Data

US 2010/0227296 A1    Sep. 9, 2010

Related U.S. Application Data

(60) Provisional application No. 61/202,499, filed on Mar. 5, 2009.

(51) Int. Cl.
*A61C 5/00* (2006.01)

(52) U.S. Cl.
USPC .......................................................... 433/215

(58) Field of Classification Search ............... 433/29, 433/37, 215, 229
See application file for complete search history.

(56) References Cited

U.S. PATENT DOCUMENTS

| | | | |
|---|---|---|---|
| 5,880,826 A * | 3/1999 | Jung et al. ................. | 356/73 |
| 6,584,341 B1 | 6/2003 | Mandelis et al. | |
| 2003/0011191 A1* | 1/2003 | Tosaki et al. .............. | 283/115 |
| 2005/0027172 A1 | 2/2005 | Benavides et al. | |
| 2005/0038678 A1 | 2/2005 | Qian et al. | |
| 2005/0228692 A1 | 10/2005 | Hodgdon | |
| 2006/0129427 A1 | 6/2006 | Wennberg | |
| 2007/0021670 A1 | 1/2007 | Mandelis et al. | |

FOREIGN PATENT DOCUMENTS

| WO | 97/50046 | 12/1997 |
|---|---|---|
| WO | 2009/156936 | 12/2009 |

OTHER PUBLICATIONS

"Taking Preventive Measures to Protect Tomorrow's Smiles", 3M ESPE, Preventive Measures Oral Health Risk Assessment and Management, 12 pages.
"Oral Health Risk Assessment Test", 3M ESPE , Preventive Measures Risk Assessment and Management Program, 1 page.
"Taking Preventive Measures to Protect Tomorrow's Smiles", 3M ESPE, Preventive Measures Risk Assessment and Management Guide, 2 pages.
"AAPD Caries-Risk Assessment Tool (CAT)*", 1 page, 2-OH-013 (May 2006).
"Caries Risk Assessment Tool", First Dental Home, Texas Department of State Health Services, 1 page, EF08-12880 Rev-0208.
"University of Iowa Caries Risk Assessment", Caries Risk Factors & Activity Assessment, 3 pages.

(Continued)

*Primary Examiner* — Cris L Rodriguez
*Assistant Examiner* — Hao D Mai
(74) *Attorney, Agent, or Firm* — Lynn C. Schumacher; Hill & Schumacher

(57) ABSTRACT

A method of oral health risk assessment is provided in which diagnostic data from an oral health detection device and patient risk factor data is processed to provide a integrated risk measure relating to a patient's dental health. The patient risk factor data preferably includes risk factor data such as pathological risk factors, protective risk factors, historical factors, self care factors, behavioral factors, and extrinsic factors. The integrated risk assessment and patient data is preferably provided to a remote server for access by various authorized stakeholders.

55 Claims, 8 Drawing Sheets

OTHER PUBLICATIONS

"Table 2—Caries Risk Assessment", Modified from American Dental Association Council on Access, Prevention and International Relations, Niessen & DeSpain, and Rethman.

KJ Anusavice, "Caries Risk Assessment", Operative Dentistry Supplement 6, 2001, pp. 19-26.

J.W. Stamm, "Risk Assessment for Oral Diseases", Adv Dent Res 5, Dec. 1991, pp. 4-17.

Rethman, "Trands in Preventive Care: Caries Risk Assessment and Indications for Sealants", JADA, vol. 131, Jun. 2000, pp. 8S-12S.

Kevin J. Hale et al., "Oral Health Risk Assessment Timing and Establishment of the Dental Home", Pediatrics, vol. 111, No. 5, May 2003, pp. 1113-1116.

"Taking Preventive Measures to Protect Tomorrow's Smiles", 3M ESPE, Preventive Measures Oral Health Risk Assessment and Management, 12 pages, Copyright 3M 2009 (p. 12).

"Oral Health Risk Assessment Test", 3M ESPE, Preventive Measures Risk Assessment and Management Program, 1 page, Copyright 3M 2009.

"Taking Preventive Measures to Protect Tomorrow's Smiles", 3M ESPE, Preventive Measures Risk Assessment and Management Guide, 2 pages, Copyright 3M 2009.

Alian, et al., "Assessment of Caries Risk in Elderly Patients Using the Cariogram Model", JCDA, Jun. 2006, vol. 72, No. 5, pp. 459-463d.

Young, et al., "Caries Management by Risk Assessment: Implementation Guidelines", CDA Journal, vol. 35, No. 11, Nov. 2007, pp. 799-805.

Ramos-Gomez, et al., "Caries Risk Assessment Appropriate for the Age 1 Visit (Infants and Toddlers)", CDA Journal, vol. 35, No. 10, Oct. 2007, pp. 687-702.

"Policy Statement on the Use of a Caries-Risk Assessment Tool", Adopted 2002, Council on Clinical Affairs, 7 pages.

"Caries Risk Assessment Form for Age 0 to 5 Years", California Dental Association, 2002, 4 pages.

"Caries Risk Assessment Form for Children 6 Years and Older/Adults", California Dental Association, 2002, 4 pages.

"Fluoride Treatments for the life of your teeth", Oral-B Laboratories, 2001, 1 page, ESA 3476 Rev. 06/01.

\* cited by examiner

Clinical Data Collection Worksheet
Date

Subject ID:_____ Initials:_____

DENTAL HISTORY (Risks)

Frequency of Brushing (daily)
    ___None
    ___Once
    ___Twice
    ___Three times
    ___More than three times Uses Fluoride tooth paste    ___Yes    ___No Tooth paste type
    ___Aim
    ___ProHealth
    ___Prevident
    ___Sensodyne
    ___Whitening tooth pastes
    ___Other (specify):_____

Gums bleed when brushing or flossing    ___Yes    ___No

Flosses (Daily)    ___Yes    ___No

FIGURE 3

|  |  | Risk Measure from Diagnostic Data |  |  |
|---|---|---|---|---|
|  |  | Healthy | Somewhat healthy | Unhealthy |
| Risk Measure from Patient Risk Factor Data | Low | OK | OK | treatment |
|  | Medium | OK | Put in observation | treatment |
|  | High | OK | Treatment | treatment |

FIGURE 4

METHOD OF ASSESSING ORAL HEALTH RISK

CROSS-REFERENCE TO RELATED APPLICATION

This application claims priority to U.S. Patent Application No. 61/202,499, filed on Mar. 5, 2009, titled "INTEGRATED ORAL DIAGNOSTIC DEVICE, DATA ACQUISITION AND MANAGEMENT SYSTEM FOR MONITORING ORAL HEALTH", the entire contents of which are incorporated herein by reference.

FIELD OF INVENTION

The present invention relates to diagnostic methods in dentistry, and more particularly, the present invention relates to methods of assessing oral health risk.

BACKGROUND OF THE INVENTION

The development of dental caries requires the interaction of three elements: a susceptible host, a cariogenic microbial flora and a carbohydrate rich diet [Keyes, P. H., "Recent advances in dental caries research. Bacteriology. Bacteriological findings and biological implications", International Dental Journal, 1961, Volume 12, page 443; Krasse, B., "Caries Risk. A practical guide for assessment and control", 1985, Chicago, Quintessence Publishing Company]. This multifactorial etiology should be taken into account during oral screenings. Indicators such as past caries experience, socioeconomic status, oral hygiene, diet, microbiological factors (lactobacilli, S mutans and yeasts), salivary factors (pH, flow rate, buffer capacity and viscosity) should be incorporated into any screening procedure [Pitts, N. B., "Risk assessment and Caries Prediction", Journal of Dental Education", 1998, Volume 62, #10, pages 762-770; Reich, E., Lussi, A., Newbrun, E., "Caries Risk Assessment", International Dental Journal, 1999, Volume 49, pages 15-26]. Work done by Demers et al. [Demers, M., Brodeur, J-M, Simard, P. L., Mouton, C., Veilleux, G., Frechette, S., "Caries predictors suitable for mass-screenings in children: A literature review", Community Dental Health, 1990, Volume 7, pages 11-21] concluded that a combination of several factors could provide a more efficient screening test than a single indicator. They felt past caries experience, and microbiological factors stand first because they are easy to determine, they show a reasonably good association with caries and their combination takes into account the three elements that produce caries. The risk assessment can be complemented with more accurate diagnostic methods.

Visual diagnosis of occlusal caries typically has a very low sensitivity and high specificity [ten Cate, J. M., van Amerongen, "Caries Diagnosis, Conventional Methods", in "Early Detection of Dental Caries, Stookey, G. K., editor, 1996, Indiana University, Indianapolis Ind.]. Sensitivities scatter around a value of 0.3 implying that only 20-48% of the caries present (usually into dentine) are found [Wenzel, A., Larson, M. J., Fejerskov, O, "Detection of occlusal caries without cavitation by visual inspection, film radiographs, xeroradiographs, and digitized radiographs" Caries Research, 1991, Volume 25, pages 365-371; Kidd, E. A. M., Ricketts, Dd. N. J., Pitts, N. B., "Occlusal caries diagnosis: A changing challenge for clinicians and epidemiologists", J. Dent., 1993, Volume 21, pages 323-331]. For approximal surfaces in vivo, only 22% of the surfaces detected by radiographic methods were detected "clinically" [Hansen, B. F., "Clinical and roentgenologic caries detection", Dentomaxillofacial Radiology, 1980, Volume 9, pages 34-36]. Angmar-Masson and ten Bosch in 1993 [Angmar-Mansson, B., ten Bosch, J. J., "Advances in methods for diagnosing coronal caries—A review", Adv. Dent. Res., 1993, Volume 7, #2, pages 70-79] concluded any diagnostic method is preferable to visual examination.

Peers, Mitropoulos and Holloway [[1]Peers, A., Hill, F. J., Mitropoulos, C. M., Holloway, P. J., "Validity and reproducibility of clinical examination, fibre-optic transillumination and bite-wing radiology for the diagnosis of small approximal carious lesions: An in vitro study", Caries Research, 1993, Volume 27, pages 307-311] concluded that fibreoptic transillumination and bitewing radiographs are superior to visual examination. These papers studied visual examinations done in a dental office, a much more sophisticated maneuver than an oral screening and still found that visual examination not the ultimate diagnostic tool. Thus visual examinations and for that matter visual screenings may not detect caries that need treatment immediately. A more accurate diagnostic methodology has been reported recently [Jeon R. J., Hellen A., Matvienko A., Mandelis A., Abrams S. H., Amaechi B. T., In vitro Detection and Quantification of Enamel and Root Caries Using Infrared Photothermal Radiometry and Modulated Luminescence. Journal of Biomedical Optics 13(3), 048803, 2008.].

Visual examination, radiographs, measurements or read outs from other diagnostic devices are only indicators or clinical signs that there is disease present or that there has been recent disease. [Featherstone, J. D. B., Young, D. A., et al. "Caries Risk Assessment in Practice for Age 6 through Adult", CDA Journal 25(10), 703-713, 2007]. These readings and results are a clinical observation that indicates that disease is present. These are not pathological factors but observations. When these observations are combined with the patient's health history and risk factors for developing disease then one can look at the future risk or ongoing risk for disease.

For example, a patient with frank cavities usually has a high level of cariogenic bacteria, and placing restorations does not significantly lower the overall bacterial challenge in the mouth. [Featherstone, J D B., Gansky S A., et al. "A randomized clinical trial of caries management by risk assessment" Caries Research 39(4) 295, 2005]. The evaluation of risk factors combined with more accurate diagnostic methods can assist the oral health care provider with a better means of diagnosis or assessment of the state of dental caries and other diseases of the hard and soft dental tissues, the activity of the disease and chances of the disease continuing or recurring in the future. In oral health care, the combination of these types of data does not exist. Typically devices provide images or output but this is never interpolated into a report.

SUMMARY OF THE INVENTION

In a preferred embodiment, the present invention provides a method of oral health risk assessment in which diagnostic data from an oral health device and patient risk factor data are processed to obtain an integrated risk measure.

Accordingly, in a first aspect, the invention provides a computer implemented method of determining an oral health risk status of a patient, the method comprising the steps of:

receiving diagnostic data pertaining to the patient from an oral health detection device;

receiving risk factor data pertaining to the patient;

processing the diagnostic data and the risk factor data on a processor to determine an oral health risk status of the patient, wherein the step of processing the diagnostic data and the risk factor data comprises:

determining one or more diagnostic risk measures based on the diagnostic data;

determining one or more patient risk measures based on the risk factor data; and combining the risk measures to obtain an integrated risk measure associated with said oral health risk status of the patient.

The diagnostic data is preferably compared to pre-determined risk-associated diagnostic values to obtain the diagnostic risk measure, and more preferably, each pre-determined diagnostic value has associated therewith a risk score, and where the diagnostic risk measures are obtained from the risk scores associated with the pre-determined diagnostic values closest to the diagnostic data.

The oral diagnostic device preferably detects oral health conditions including demineralization of teeth, remineralization of teeth, presence of dental caries on enamel and root surfaces, erosion, defects in restorations, defects and caries along the margins of restorations, cracks, periodontal disease, diseases of the hard and soft tissues, and oral cancer.

The patient risk factor data is preferably compared with pre-determined risk-associated risk factor values to obtain the patient risk measures, and more preferably, each pre-determined risk factor value has associated therewith a risk score, and where the patient risk measures are risk scores associated with the pre-determined risk factor values closest to the risk factor data. The patient risk factor data preferably includes pathological risk factors, protective risk factors, historical factors, self care factors, behavioral factors, and extrinsic factors.

The risk measures are combined to obtain an integrated risk measure associated with an oral health risk status of the patient by multiplying each the risk measure by a pre-determined weighing factor to obtain weighed risk measures and combining the weighed risk measures to obtain the integrated risk measure.

In another aspect, the invention provides a computer implemented method of obtaining data relating to a clinical trial for an oral product, therapy or treatment, the method comprising the steps of:

obtaining diagnostic data pertaining to a plurality of patients in the clinical trial from an oral detection device;

obtaining risk factor data pertaining to each patient of the plurality of patients;

processing the diagnostic data and the risk factor data on a processor to determine said oral health risk status of the each patient, wherein the step of processing the diagnostic data and the risk factor data comprises:

determining one or more diagnostic risk measures based on the diagnostic data;

determining one or more patient risk measures based on the risk factor data; and combining the risk measures to obtain an integrated risk measure associated with said oral health risk status of the each patient;

administering one of a product, therapy and oral treatment to the patients; and performing steps a)-f) to obtain post-treatment integrated risk measures associated with said oral health risk status of each patient.

In yet another aspect, the invention provides a computer implemented method of determining an oral health risk assessment for a patient population, the method comprising the steps of:

obtaining diagnostic data pertaining to each patient in the patient population with an oral health detection device;

obtaining risk factor data pertaining to each patient;

processing the diagnostic data and the risk factor data on a processor to determine said oral health risk status of the each patient, wherein the step of processing the diagnostic data and the risk factor data comprises:

determining one or more diagnostic risk measure based on the diagnostic data;

determining one or more patient risk measure based on the risk factor data; and combining the risk measures to obtain an integrated risk measure associated with said oral health risk status of the each patient.

In a further aspect, the invention provides a system for determining an oral health risk status of a patient, the system comprising:

a data interface for receiving diagnostic data from an oral detection device and risk factor data, wherein the diagnostic data and the risk factor data pertains to the patient;

a processor for processing the diagnostic data and the risk factor data to determine said oral health risk status of the patient, the processor programmed with computer-readable instructions to:

determine one or more diagnostic risk measures based on the diagnostic data;

determine one or more patient risk measure based on the risk factor data; and combine the risk measures to obtain an integrated risk measure associated with said oral health risk status of the patient; and an output means for one of displaying, recording, and exporting the integrated risk measure.

In yet another aspect, the invention provides a method of determining a health status of an oral tissue, the method comprising the steps of:

a) irradiating the tissue with an optical beam;

b) measuring a photothermal (PTR) signal comprising an amplitude and phase signal from the tissue;

c) measuring a luminescence (LUM) signal comprising an amplitude and phase signal from the tissue;

d) comparing the signals with reference signals; and e) determining a health status measure based one the comparison.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which:

FIG. 3 is a sample of a section of a case report form that provides the health and social history of the patient and some of the know risk factors;

FIG. 4 is an example of a decision matrix for risk factors and data from the diagnostic device;

DETAILED DESCRIPTION OF THE INVENTION

Generally speaking, the embodiments described herein are directed to method of oral health risk assessment. As required, embodiments of the present invention are disclosed herein. However, the disclosed embodiments are merely exemplary, and it should be understood that the invention may be embodied in many various and alternative forms.

The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, a method of oral health risk assessment using data from a photothermal radiometric and luminescence based diagnostic device is disclosed herein.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

As used herein, the terms "about", and "approximately" when used in conjunction with ranges of dimensions, concentrations, temperatures or other physical or chemical properties or characteristics is meant to cover slight variations that may exist in the upper and lower limits of the ranges of properties/characteristics.

As used herein, the coordinating conjunction "and/or" is meant to be a selection between a logical disjunction and a logical conjunction of the adjacent words, phrases, or clauses. Specifically, the phrase "X and/or Y" is meant to be interpreted as "one or both of X and Y" wherein X and Y are any word, phrase, or clause.

Figure 1:
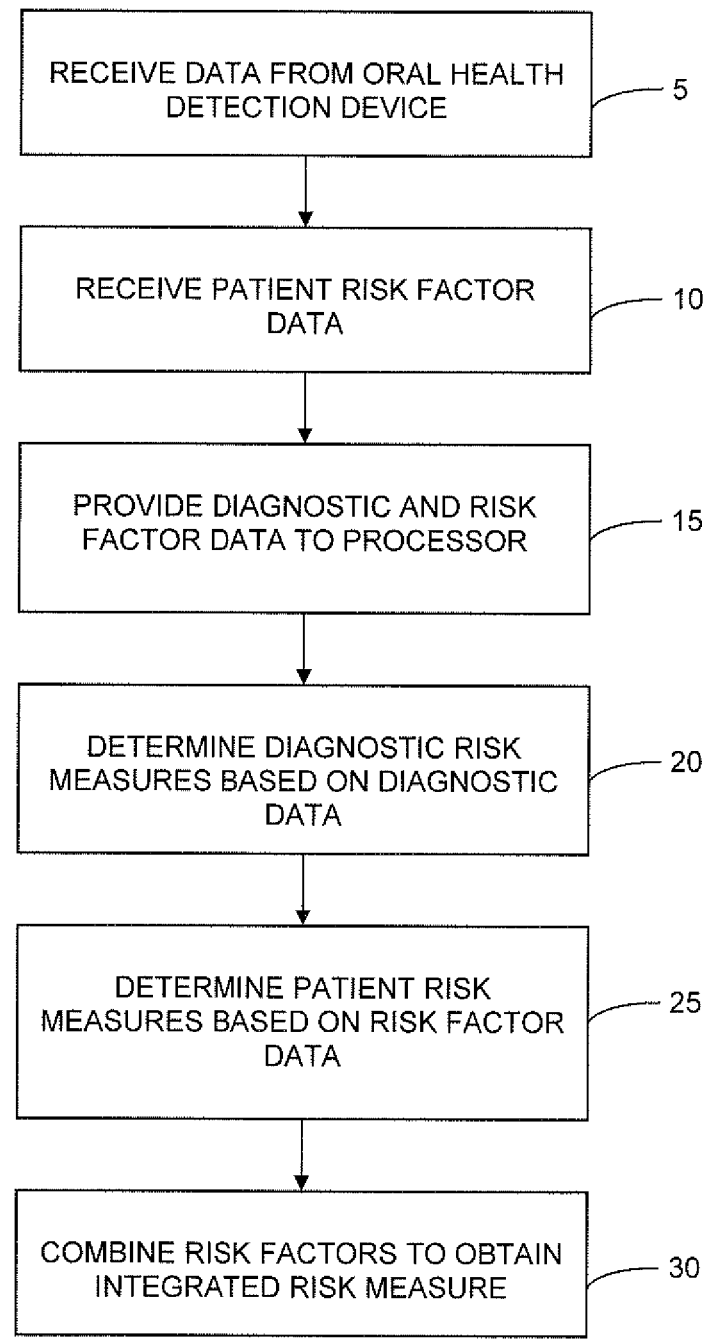
FIG. 1 is illustrates a method of processing diagnostic data and patient risk factor data to obtain an integrated risk measure for the oral health of a patient.

Referring to FIG. 1, a method is provided for the assessment of oral health risk in which both diagnostic data and patient risk factor data are combined to provide an integrated risk measure. Diagnostic data from an oral health detection device is received in step 5 and data describing patient risk factors is also received in step 10. This data is then provided to a processor in step 15, which determines diagnostic risk measures related to the diagnostic data in step 20 and patient risk measures related to the patient risk factor data in step 25. In step 30, the processor combines the risk measures to obtain an integrated oral health risk assessment comprising an integrated risk measure. The integrated risk measure is preferably provided with patient identification information, and may be stored in an electronic patient record, paper record or database system.

The oral health diagnostic device is used for capturing of data indicative of the health or disease present in a tooth and supporting structure (hard and soft tissues in the oral cavity) including information on dental caries, cracks, erosion lesions, restorations, periodontal disease and other diseases of the hard and soft tissues. In one embodiment, the data is obtained by scanning of a tooth surface using the dental diagnostic device for the detection and monitoring of dental caries, erosion, secondary caries and capturing of this data and other relevant information used in the dental diagnostic device. This data is then stored in a device in association with identifying information such as patient ID, tooth and/or site examined. Several non-limiting examples of oral health detection devices are provided below.

The oral health diagnostic data preferably comprises quantitative data indicative of the presence or absence of one or more oral health conditions. More preferably, the oral health diagnostic data comprises data indicative of the severity of one or more oral health conditions. The data may include images of the tooth surfaces being examined. Exemplary yet non-limiting conditions include of demineralization of teeth, remineralization of teeth, presence of dental caries on enamel, presence of dental caries root surfaces, erosion, defects in restorations, defects and caries along the margins of restorations, cracks, periodontal disease, diseases of the hard and soft tissues, and oral cancer. Additionally, the device may detect changes associated with the health of a tooth, such as demineralization of the enamel surface, demineralization of the root surface, remineralization of the root surface, remineralization of the enamel surface, and restoration in or on the tooth or its surrounding tissue. The diagnostic data is also preferably provided with information pertaining to the oral location from where the measured data was obtained. Those skilled in the art will appreciate that a wide variety of oral health detection devices are compatible with embodiments of the invention.

The oral health diagnostic device may employ an optical signal for the measurement of a dental health condition. Such optical signals include, but are not limited to, luminescence, fluorescence, and thermal emission. Such optical signals may be at various frequencies. Many important biological objects containing fluorescing components (fluorophores) exhibit intrinsic fluorescence (or autofluorescence). In dentistry, the aim of recent scientific research has been the use of laser fluorescence for detection of tooth demineralization (e.g. enamel and/or root), dental deposits, and dental calculus and quantitative analysis of lesion depth and size, as well as the mineral composition of the enamel [M. L. Sinyaeva, Ad. A. Mamedov, S. Yu. Vasilchenko, A. I. Volkova, and V. B. Loschenov, 2003, "Fluorescence Diagnostics in Dentistry", Laser Physics, 14, No. 8, 2004, pp. 1132-1140].

UV radiation (488 nm) has been used to examine dental enamel [Susan M. Higham, Neil Pender, Elbert de Josselin de Jong, and Philip W. Smith, 2009. Journal of Applied Physics 105, 102048, R. Hibst and R. Paulus, Proc. SPIE 3593, 141 (1999)]. The studies showed that autofluorescence of healthy enamel were peaked at a wavelength of 533 nm, whereas the autofluorescence of carious tissue was red-shifted by 40 nm. It was also demonstrated that the autofluorescence intensity of carious zones was an order-of-magnitude lower than the autofluorescence intensity of a healthy tooth in spite of the fact that the absorbance of the carious zone at the excitation wavelength was significantly higher.

The reduction in fluorescence when enamel demineralizes has been attributed to the increase in porosity of carious lesions when compared with sound enamel. There is an associated uptake of water and decrease in the refractive index of the lesion resulting in increased scattering and a decrease in light-path length, absorption, and autofluorescence [H. Bjelkhagan, F. Sundström, B. Angmar-Månsson, and H. Ryder, Swed Dent. J. 6, 1982].

At long wavelengths excitation, the autofluorescence intensity of a carious cavity can be higher than the autofluorescence intensity of healthy tissue [R. Hibst et al.]. For excitation wavelengths of 640 or 655 nm, the integral (at wavelengths greater than 680 nm) autofluorescence intensity of a carious cavity could be approximately one order-of-magnitude greater than the corresponding integral autofluorescence intensity of healthy enamel. There is some indication that the induced fluorescence with these wavelengths results from the excitation of fluorescent fluorophores from bacterial metabolites. These fluorophores are thought to originate from porphyrins found in some bacterial species [S. M. Higham et al.].

Accordingly, in one embodiment, the diagnostic data may be provided by an oral health detection device such as, but not limited to, commercial dental diagnostic systems such as those offered by QLF™ and DIAGNOdent™.

More recently, a new system has been developed based on the combination of laser induced fluorescence and photothermal radiometry. The system, commercially available as The Canary Dental Caries Detection System™, which examines luminescence and photothermal effect (PTR-LUM) of laser light on a tooth. The laser is non-invasive and can detect tooth decay a fraction of a millimeter in depth and up to five millimeters below a tooth's surface. When pulses of laser light are focused on a tooth, the tooth glows and releases heat. By analyzing the emitted light and heat signatures from the tooth, very accurate information about the tooth's condition can be obtained including signs of early demineralization (lesions) of enamel [Nicolaides, L, Mandelis, A., Abrams, S. H., "Novel Dental Dynamic Depth Profilometric Imaging using Simultaneous Frequency Domain Infrared Photothermal Radiometry and Laser Luminescence", Journal of Biomedical Optics, 2000, January, Volume 5, #1, pages 31-39, Jeon, R. J., Han, C., Mandelis, A., Sanchez, V., Abrams, S. H., "Non-intrusive, Non-contacting Frequency-Domain Photothermal Radiometry and Luminescence Depth Profilometry of Carious and Artificial Sub-surface Lesions in Human Teeth," Journal of Biomedical Optics 2004, July-August, 9, #4, 809-81, Jeon R. J., Hellen A., Matvienko A., Mandelis A., Abrams S. H., Amaechi B. T., In vitro Detection and Quantification of Enamel and Root Caries Using Infrared Photothermal Radiometry and Modulated Luminescence. Journal of Biomedical Optics 13(3), 048803, 2008]. As a lesion grows, there is a corresponding change in the signal. As remineralization progresses, a signal reversal indicates an improvement in the condition of the tooth. By changing the frequency of the signal one can probe up to 5 mm. below the tooth surface. Low frequency signals can penetrate the defects and lesions beneath the tooth surface.

A hybrid PTR-LUM system according to a preferred embodiment of the invention is preferably a phase-sensitive detection system that performs four measurements per location and/or per frequency at each location:
1. PTR Amplitude: the strength of the emitted blackbody IR signal
2. LUM Amplitude: the strength of the luminescence signal
3. PTR Phase: the shift in phase of the emitted blackbody IR signal
4. LUM Phase: the shift in phase of the luminescence signal These four measurements, when combined, provide information on the status of the tooth surface and changes in the carious lesion. Alternatively, a subset of the above measurements may be combined for use with the above method, for example, combining PTR amplitude data and LUM amplitude data.

In one embodiment, the oral health detection device itself is programmed to calculate an amount of demineralization or remineralization by comparing the measured data to known standards to calculate mineral loss or mineral gain. This measurement of mineral loss or gain may then be used to measure ongoing demineralization or remineralization of the hard tissue including enamel or root surface. This measurement could then be used as part of ongoing clinical trials into the efficacy of various therapeutic measures or agents.

The processor, or the oral health detection device, may be programmed to first determine a severity of an oral condition prior to determining the diagnostic risk measures based on the diagnostic data. In a series of non-limiting examples, the severity or an oral condition may be obtained by determining one of a number of dental caries, a severity of one or more dental caries, a number of demineralization areas, a severity of one or more demineralization areas, a number of white spots, a number of brown spots, a severity of one or more white spots, a severity of one or more brown spots. In a preferred embodiment, the severity of the oral health condition is determined according to a standard or clinically accepted assessment scale.

Figure 2:
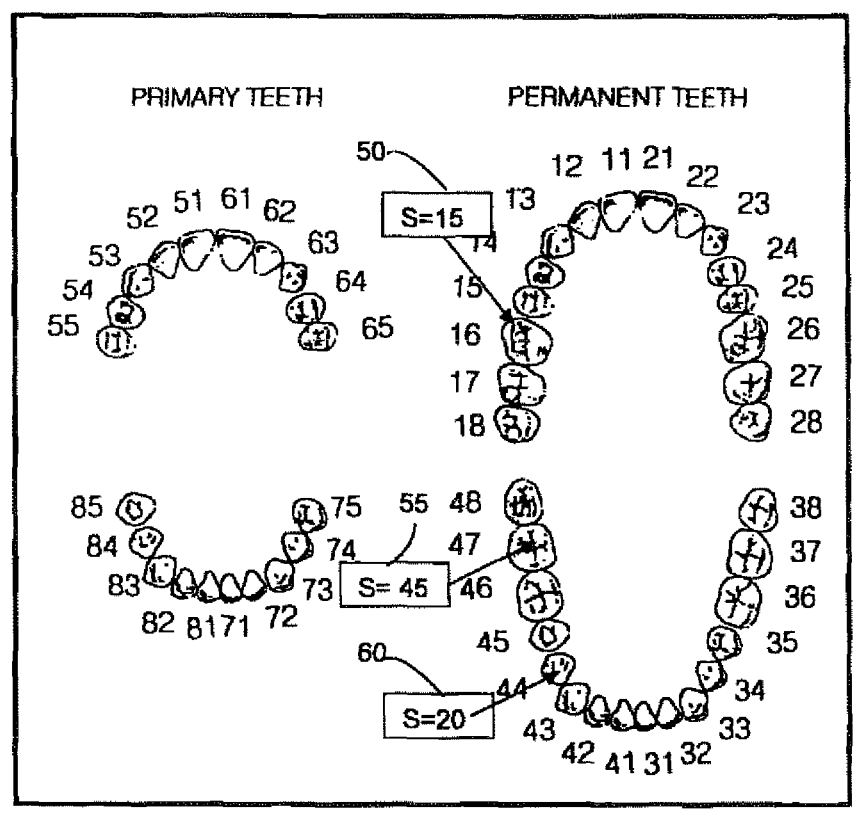
FIG. 2 is an illustration shown a patient's teeth and corresponding diagnostic data pertaining to specific teeth.

In one embodiment, the diagnostic data is received by the processor in step 15 in the form of a series of diagnostic measurements correlated with individual teeth or groups of teeth. This type of data is illustrated in FIG. 2, which provides a schematic of a patient's teeth having overlaid thereon a series of tooth-specific diagnostic measurements that are each indicative of the presence or absence of an oral health condition. Measurements 50, 55 and 60 provide integrated photothermal radiometric and luminescence data measured for three specific teeth. This data, correlated with the specific teeth and the specific patient, is provided to the processor for determination of the diagnostic risk measures. The use of photothermal radiometric data, and a method for combining a collection of photothermal and luminescence measurements to provide a single diagnostic data value, is discussed further in the examples below.

Referring again to FIG. 1, in step 20, the diagnostic risk measures related to the diagnostic data are obtained by the processor carrying out a series of computational steps in which the diagnostic data is compared to pre-determined risk-associated diagnostic values. More preferably, the diagnostic risk measures are obtained by comparing the diagnostic data to pre-determined diagnostic values and obtaining a risk score based on the comparison. The risk score may be a quantitative value, such as a score between 0 and 1, or may be selected from a list of qualitative values. In a non-limiting example, in which the measured diagnostic data is fluorescence intensity, the measured fluorescence intensity is compared with reference values, with the reference values sorted into bins, where each bin is associated with a risk score. The diagnostic risk measure is the risk score of the bin corresponding to the measured signal.

Table 1 below illustrates a non-limiting example in which a categorization method is provided by which data from a photothermal and luminescence detection device may be processed to obtain a qualitative risk measure for a series of risk-based questions.

TABLE 1

Determination of Risk Measures from Diagnostic Data

| Questions | Risk Category (See Table 3) | Risk Factor (See Table 3) | Observations/Data (normalized data) | Converted to Risk Measure: |
|---|---|---|---|---|
| What is the PTR Amplitude per tooth surface? | Device Reading - MS | a - PTR Amplitude per Tooth Surface (in microvolts) - ONS | 8 to 15 | Satisfactory |
| | | | 20 to 30 | Fairly Satisfactory |
| | | | 60 to 90 | Borderline |
| | | | | Not Very Satisfactory |
| | | | | Unsatisfactory |
| What is the LUM Amplitude? | Device Reading - MS | LUM Amplitude - ONS | 6 to 10 | Satisfactory |
| | | | 1 to 5 | Fairly Satisfactory |
| | | | less than 1 | Borderline |
| | | | | Not Very Satisfactory |
| | | | | Unsatisfactory |
| How many PTR & LUM Amplitudes indicate healthy? | Device Reading - MS | # of PTR & LUM Amplitudes Indicating Healthy - MS | | Satisfactory |
| | | | 2 | Fairly Satisfactory |
| | | | 3 | Borderline |
| | | | 4 or more | Not Very Satisfactory |
| | | | | Unsatisfactory |
| How many PTR & LUM Amplitudes indicate brown spots? | Device Reading - MS | # of PTR & LUM Amplitudes Indicating Brown Spots - MS | 0 | Satisfactory |
| | | | 2 | Fairly Satisfactory |
| | | | 3 | Borderline |
| | | | 4 or more | Not Very Satisfactory |
| | | | | Unsatisfactory |
| How many PTR & LUM Amplitudes indicate caries spots? | Device Reading - MS | # of PTR & LUM Amplitudes Indicating Caries Spots - MS | 0 | Satisfactory |
| | | | 2 | Fairly Satisfactory |
| | | | 3 | Borderline |
| | | | 4 or more | Not Very Satisfactory |
| | | | | Unsatisfactory |

The first two questions involve the amplitude of the measured PTR and LUM signals measured per tooth surface. This raw observation data is processed by the processor to determine the observation data for the remaining questions by comparing the signals to a set of criteria indicating the presence or absence of health tissue, spots and caries. The answers to the questions are binned according to the "Observations/Data" column, which determines the corresponding risk assessment value. For example in the final question, titled "How many PTR & LUM Amplitudes indicate caries spots", a to value of 3 is considered to be "Not Very Satisfactory", which indicates an increased risk of an oral health condition.

The above description provided methods for obtaining risk measures based on the diagnostic data. As shown in FIG. 1, the method summarized by the flow chart further includes providing one or more patient risk factors to the processor prior to the determination of the integrated risk measure. These patient risk factors are not directly measured by the diagnostic device (although they can be input by an input means connected to the device, such as a keyboard and mouse, voice activated software and data input systems), but instead constitute additional tertiary factors that can impact the risk of developing an oral health condition. According to a preferred embodiment, when this patient-specific risk factor data is combined with the diagnostic data discussed above, a powerful tool is obtained for predicting future risk of a patient encountering future oral health problems including dental caries.

In a preferred embodiment, the patient risk factors relate to one or more of pathological risk factors, protective risk factors, historical factors, behavioural and or extrinsic factors. The pathological risk factors may include, but are not limited to, a plaque index, quantity of existing tooth decay, size of existing tooth decay, distribution of existing tooth decay, presence of acidogenic or pathologic bacteria, reduced salivary flow, bleeding of gums when brushed or flossed, number of decayed, missing or filled teeth, crowding or mal-alignment of the teeth and frequency of carbohydrate ingestion. The historical risk factors may include, but are not limited to, an integrity of a tooth surface, a status of oral tissues, a history of grinding teeth, exposed root surfaces, number of years living in a fluoridated community, and a number within a prescribed period of fillings, root canals, crowns, bridges, partial dentures, tooth extractions, oral and periodontal surgical procedures and implants.

The protective risk factors may include, but are not limited to, use of remineralization agents, an amount of salivary flow, the presence of salivary components comprising one or more of proteins, calcium, phosphate, fluoride, immunoglobins, and antibacterials in saliva. Behavioral risk factors may include, but are not limited to, chewing gums and consumption of dairy products, consumption of carbohydrates and tendency to grind teeth.

Self-care risk factors may include, but are not limited to, frequency of tooth brushing, timing of oral health maintenance including brushing or flossing, frequency of tooth flossing, manual dexterity and ability to properly use various oral health aids properly including a tooth brush, use of a fluoridated toothpaste, use of other oral health home care aids, and use of selected mouth rinses.

Furthermore, the extrinsic risk factors may include, but are not limited to, diet, sufficiency of home care, access to oral care, gender, age, geographic location, socio-economic status and one or more demographic factors.

A non-limiting example of a patient intake form including several patient risk factor questions is shown in FIG. 3. The patient risk factors may additionally or alternatively be obtained from available oral health risk assessment tools including, but not limited to, tables, surveys, scales, and questionnaires. For example, patient risk factors may be obtained from oral health risk assessment tools including the University of Iowa Caries Risk Assessment Tool, the American Academy of Pediatric Dentistry Caries Risk Assessment Tool, the Texas Department of State Health Services Caries Risk Assessment Tool, the California Dental Association Caries Risk Assessment Forms, and tools available from dental product companies such as Crest and Colgate.

In a preferred embodiment, the patient risk measures related to the patient risk factor data are obtained by the processor carrying out a series of computational steps in which the patient risk factor data is compared to pre-determined risk-associated risk factor values to obtain the patient risk measures. More preferably, the one or more patient risk measures are obtained by comparing the risk factor data to pre-determined risk factor values and obtaining a risk score based on the comparison.

Table 2 below illustrates a non-limiting example in which a categorization method is provided by which patient risk factor data may be processed to obtain a qualitative risk measure for a series of risk-based questions.

TABLE 2

Determination of Risk Measures from Patient Data

| Questions | Risk Category | Risk Factor (See Table 3) | Observations/ Data | Converted to Risk Measure: |
|---|---|---|---|---|
| How old are you today? | Patient Profile | Age - ONS | 0 to 12 | Satisfactory |
| | | | 13 to 20 | Fairly Satisfactory |
| | | | 21 to 40 | Borderline |
| | | | 41 to 60 | Not Very Satisfactory |
| | | | 61+ | Unsatisfactory |
| Where do you live? | Patient Profile | City | | |
| How long ago was your last preventative treatment visit? | Dental Preventative Treatment History - VHS | Date of Last Preventative Visit - HS | Less than one year - or 2 per year | Satisfactory |
| | | | Greater than one year | Fairly Satisfactory Borderline Not Very Satisfactory Unsatisfactory |
| How often do you visit your dentist? | Dental Preventative Treatment History - VHS | Frequency of Dental Visit - HS | 1 to 2 per year | Satisfactory |
| | | | 3 to 4 per year | Fairly Satisfactory Borderline Not Very Satisfactory Unsatisfactory |
| Have you had | Dental Preventative | Remineralization | No | Satisfactory |

TABLE 2-continued

Determination of Risk Measures from Patient Data

| Questions | Risk Category | Risk Factor (See Table 3) | Observations/ Data | Converted to Risk Measure: |
|---|---|---|---|---|
| Remineralization therapy? | Treatment History - VHS | Therapy - CS | | |
| | | | Yes | Fairly Satisfactory Borderline Not Very Satisfactory Unsatisfactory |
| How many direct placed restorations have you had in the last 3 years? | Dental Treatment History - VHS | Number of Direct Placed Restorations in Last 3 Years - MS | 0 | Satisfactory |
| | | | 0 to 3 | Fairly Satisfactory Borderline |
| | | | 4 to 6 | Not Very Satisfactory |
| | | | 7+ | Unsatisfactory |
| How many Endodontic treatments have you had in the last 3 years? | Dental Treatment History - VHS | Number of Endodontic Treatments in Last 3 Years - MS | 0 | Satisfactory |
| | | | 1 | Fairly Satisfactory Borderline |
| | | | 2+ | Not Very Satisfactory Unsatisfactory |
| How many crowns or bridges have you had in the last 3 years? | Dental Treatment History - VHS | Number of Crowns & Bridges in Last 3 Years - CS | | Satisfactory |
| | | | 0 to 1 | Fairly Satisfactory |
| | | | 2 to 3 | Borderline Not Very Satisfactory |
| | | | 4+ | Unsatisfactory |
| Do you have a partial denture? | Dental Treatment History - VHS | Type of Partial Dentures - CS | No | Satisfactory |
| | | | Yes | Fairly Satisfactory Borderline Not Very Satisfactory Unsatisfactory |
| Do you have a history of clenching or bruxing? | Oral Tissue Status - HS | History of Clenching or Bruxing - VHS | No | Satisfactory |
| | | | Yes | Fairly Satisfactory Borderline Not Very Satisfactory Unsatisfactory |

TABLE 2-continued

Determination of Risk Measures from Patient Data

| Questions | Risk Category | Risk Factor (See Table 3) | Observations/ Data | Converted to Risk Measure: |
|---|---|---|---|---|
| Do you have any exposed roots? | Oral Tissue Status - HS | Presence of Exposed Root - HS | No | Satisfactory |
| | | | Yes | Fairly Satisfactory Borderline Not Very Satisfactory Unsatisfactory |
| Do you have malocclusion or crowding? | Oral Tissue Status - HS | c - Malocclusion or Crowding - AAS | No | Satisfactory |
| | | | Yes | Fairly Satisfactory Borderline Not Very Satisfactory Unsatisfactory |
| What is your saliva consistency? | Oral Tissue Status - HS | Saliva Consistency - AAS | Thick ropy | Borderline |
| | | | Normal | Satisfactory |
| | | | Drooling | Borderline |
| How often per day do you brush your teeth? | Oral Hygiene/ Home Care - MS | Frequency of Tooth Brushing - MS | three times per day or more | Satisfactory |
| | | | twice per day | Fairly Satisfactory |
| | | | once per day | Borderline Not Very Satisfactory Unsatisfactory |
| Do you use fluoridated tooth paste? | Oral Hygiene/ Home Care - MS | Use of Fluoridated Tooth Paste - MS | Yes | Satisfactory |
| | | | No | Fairly Satisfactory Borderline Not Very Satisfactory Unsatisfactory |
| Do your gums bleed when you brush or floss? | Oral Hygiene/ Home Care - MS | Gum Bleeding When Brushing or Flossing - MS | No | Satisfactory |
| | | | Yes | Fairly Satisfactory Borderline Not Very Satisfactory Unsatisfactory |
| Do you live in a fluoridated community? | Oral Hygiene/ Home Care - MS | Living in Fluoridated Community - MS | Yes | Satisfactory |
| | | | No | Fairly Satisfactory Borderline Not Very Satisfactory Unsatisfactory |
| Do you chew gum or eat mints? | Diet Factors - VHS | Gum Chewing and Mints - CS | No | Satisfactory |
| | | | Yes | Fairly Satisfactory Borderline |

TABLE 2-continued

Determination of Risk Measures from Patient Data

| Questions | Risk Category | Risk Factor (See Table 3) | Observations/ Data | Converted to Risk Measure: |
|---|---|---|---|---|
| Do you chew sugar free gum or sugar free mints? | Diet Factors - VHS | Sugar Free Gum & Mints - CS | No | Not Very Satisfactory Unsatisfactory Satisfactory |
| | | | Yes | Fairly Satisfactory Borderline Not Very Satisfactory Unsatisfactory |
| Do you use Xylitol or Recaldent gum or mints? | Diet Factors - VHS | Xylitol or Recaldent ™ Gum or Mints - AAS | Yes | Satisfactory |
| | | | No | Fairly Satisfactory Borderline Not Very Satisfactory Unsatisfactory |
| How often per day do you eat snacks? | Diet Factors - VHS | Snack Consumption - VHS | less than 3 per day | Satisfactory |
| | | | 3 per day | Fairly Satisfactory Borderline Not Very Satisfactory |
| | | | more than 3 per day | Unsatisfactory |
| How many cans of pop or sport drinks do you consume per day? | Diet Factors - VHS | Consumption of Pop or Sport Drinks - VHS | less than 1 can per day | Satisfactory |
| | | | 1 can per day | Fairly Satisfactory Borderline |
| | | | 2 cans per day | Not Very Satisfactory |
| | | | 3 or more cans per day | Unsatisfactory |
| Do you consume dairy products every day? | Diet Factors - VHS | Daily Dairy Consumption - HS | Yes | Satisfactory |
| | | | No | Fairly Satisfactory Borderline Not Very Satisfactory Unsatisfactory |
| What is the DMFT? | Oral Disease Indicators - VHS | DMFT - VHS | less than 5% | Satisfactory |
| | | | 5% to 10% | Fairly Satisfactory Borderline Not Very Satisfactory |
| | | | 11% or more | Unsatisfactory |
| What is the DMFS? | Oral Disease Indicators - VHS | DMFS - VHS | less than 5% | Satisfactory |

TABLE 2-continued

Determination of Risk Measures from Patient Data

| Questions | Risk Category | Risk Factor (See Table 3) | Observations/ Data | Converted to Risk Measure: |
|---|---|---|---|---|
| | | | 5% to 10% | Fairly Satisfactory Borderline Not Very Satisfactory |
| | | | 11% or more | Unsatisfactory |
| What is your plaque index? | Oral Disease Indicators - VHS | Plaque Index - VHS | 0 | Satisfactory |
| | | | 1 | Fairly Satisfactory |
| | | | 2 | Borderline |
| | | | 3 | Not Very Satisfactory Unsatisfactory |

The risk measures shown in Tables 1 and 2 are then processed to obtain a single integrated risk measure. In one non-limiting example, a numerical value is attributed to each qualitative risk measure, and the values for each risk measure are averaged to obtain the integrated risk measure. In a preferred embodiment, the risk measures are weighted prior to being processed in order to obtain a clinically significant integrated risk measure. Although data weighing may be achieved by many different methods known in the art, the present embodiment provides a non-limiting example in which the risk factors are weighed according to the weighing factors described in Table 3.

TABLE 3

Weighing Factors

| Weighing Factor | Significance |
|---|---|
| ONS | Of No Significance |
| OVLS | Of Very Little Significance |
| OLS | Of Little Significance |
| WRAS | Well Below Average Significance |
| BAS | Below Average Significance |
| AS | Average Significance |
| AAS | Above Average Significance |
| CS | Considerable Significance |
| HS | Heavy Significance |
| VHS | Very Heavy Significance |
| MS | Maximum Significance |

Referring again to Tables 1 and 2, these weighing factors are applied to each risk category to determine the degree to which a given risk category is weighed when calculating a risk measure based on the answers. Preferably, as further shown in Tables 1 and 2, the risk factors are also weighed using the weighing factors shown in Table 3. Accordingly, a given risk measure is weighed by both a weighing factor applied for the risk category, and a weighing factor applied for the risk factor. In a non-limiting example, this may be quantitatively achieved by assigning a numerical value to each weighing factor in Table 3, for example, from 0 to 10 (with zero associated with ONS), and assigning a numerical value to each risk measure, for example, with 0 representing "satisfactory" and 10 representing "unsatisfactory".

Having obtained risk measures related to both the diagnostic data and the patient risk factor data, the risk measures may be processed to obtain an integrated risk measure as described in step 30 of FIG. 1. It is to be understood that the risk measures may be combined using a variety of methods. In a preferred embodiment, in which the diagnostic risk measures and the patient risk measures are weighed, the integrated risk measure is obtained as the sum or average of the risk measures. For example, the integrated risk measure may be obtained by multiplying each risk measure by the two weighing factors for the risk category and risk factor, summing the weighted risk measures, and normalizing the value to a preferred value, such as 1 or 10. In a more preferred embodiment, additional weighing factors may be applied to the risk measures prior to performing the average in order to increase the relative weight of the diagnostic data or patient risk factor data.

The integrated risk measure, and optionally the risk measures related to the diagnostic data and the patient risk factor data, is subsequently recorded and/or outputted (preferably with a patient identifier). For example, the risk measures may be displayed on a display device such as a monitor, printed with a printer, or graphed. In a preferred embodiment, the integrated risk measure is shown in a graphical form. The risk measures are preferably provided for a patient's record, and more preferably electronically transmitted to a patient's electronic record. The risk measures may also be provided graphically. As noted above, the integrated risk measure may assist the oral health care provider with a diagnosis or assessment of the state of health of the particular tooth, soft or hard tissue, presence of dental caries, erosion, defects in restorations, or presence of periodontal disease. The combination of data from the risks factors and the output from the dental detection device yield composite information, such that each subset of data alone can not yield.

In yet another embodiment, a treatment recommendation may be provided by the processor based on the risk measures. FIG. 4 illustrates a non-limiting example of a treatment recommendation decision matrix based on the risk measures obtained according to the aforementioned method.

Figure 5:
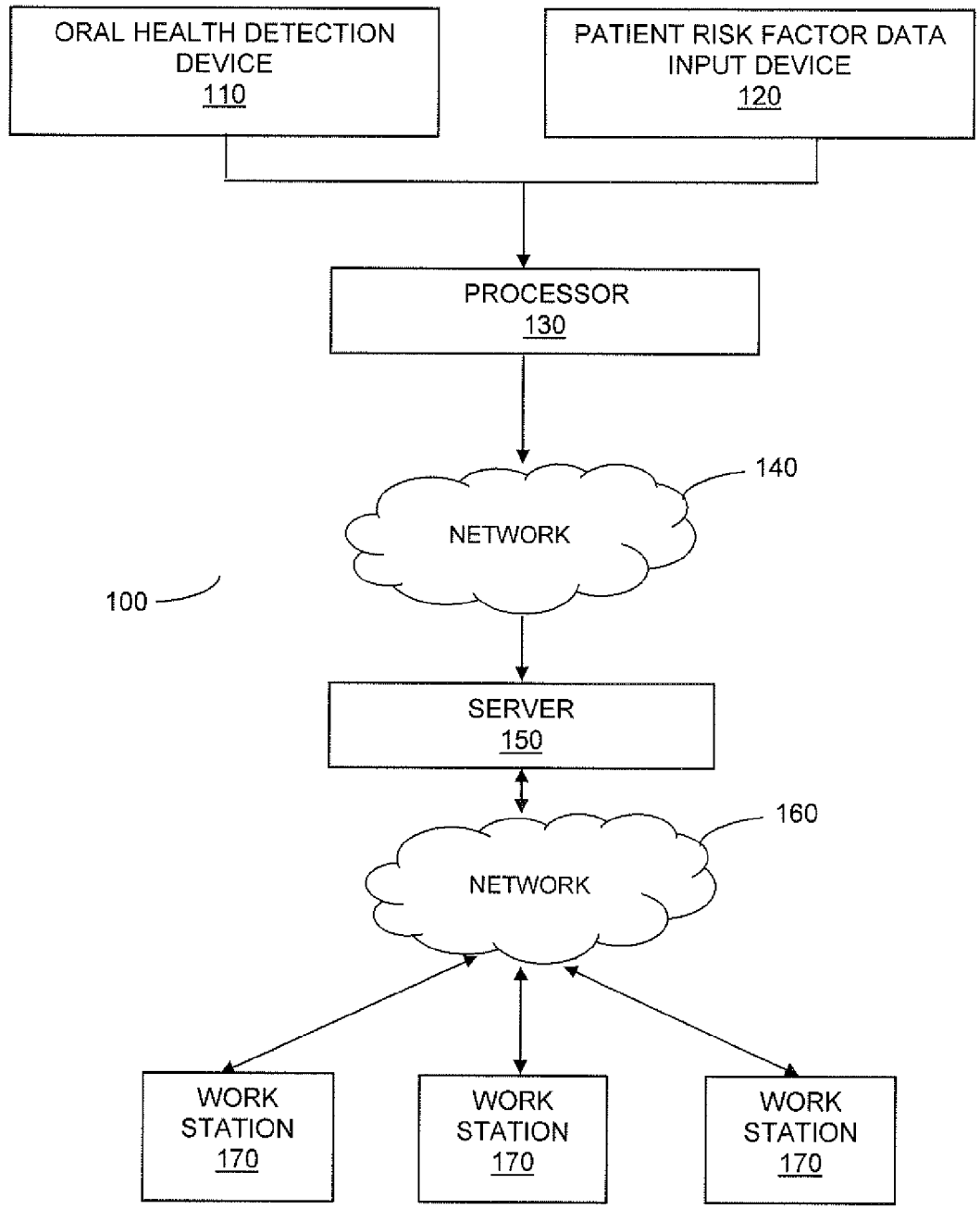
FIG. 5 illustrates a block diagram of the dental data management system in accordance with the present invention.

FIG. 5 illustrates a block diagram of an integrated oral diagnostic device and data acquisition and management system 100 for performing the above method. The system includes an oral health detection device 110, a patient risk factor data input device 120, and a data processor 130. Diagnostic data from the oral health detection device 110 and patient risk factor data from the patient risk factor input device 120 is provided to the processor, where in one embodiment, the method according to the flow chart in FIG. 1 may be executed. In a non-limiting example, the patient risk factor data input device 120 may be a personal computer or a data entry kiosk equipped with a data input apparatus such as a keyboard and mouse, a touchscreen device, or a voice activated software and/or data input system. In another example, the input device may be a remote input device connected to the system through a network, such as a personal computer accessing a web page for patient-specific risk factor data entry.

The oral health detection system and the patient risk factor input devices are preferably directly or indirectly connected to the processor 130. In one embodiment, the processor 130 resides in a computer or computing device that is physically local to at least one of the devices. For example, the oral health detection device 110, data entry device 120, and processor 130 may all reside within a dental clinic. In another embodiment, the devices 110 and 120 may be connected to the processor through either a local or a remote network (not shown in FIG. 5). In one embodiment, the processor 130 is connected to the devices through the internet, and the method according to the flowchart shown in FIG. 1 is performed at a remote location relative to the patient and/or devices.

In a preferred embodiment, the processor 130 is connected to a sever 150 for the storage, management, and delivery of patient data and risk assessment data. This may be achieved through a network 140 such as a local network, for example, a server residing within a local clinical environment having a local network, or through a remote network such as the internet. Various networking equipment (not shown) known to those skilled in the art may be included in the system to provide the desired network functionality.

Server 150 may be further connected to one or more remote computing workstations 170, such as remote personal computers, for providing remote access to patient data and risk assessment data through a network 160 such as the Internet. Alternatively server may be remotely connected to two or more systems including devices 110 and 120, enabling server 150 to service multiple clinical environments. In an alternative embodiment, the workstations 170 may comprise a cloud computing environment.

The dental diagnostic device 110 is preferably located at one or more clinical patient stations in an oral health provider's office, field setting, laboratory or medical clinic. Device 110 preferably acquires and stores the patient personal information and diagnostic data in its internal computer. System 100 may further comprise a data interface for processing the information and data from device 110 into a message or collection of data packets in form adaptable for transmission (for example, via the internet) to a server 150 that can be located nearby or remotely. Communication to the server 150 may be done via physical lines or wireless connection or other electronic means.

The server 150 receives patient data and risk assessment data, and also preferably conveys the patient and device information to one or more workstations 170 operated by various users such as, but not limited to, patients, dentists, researchers, academic institutions, and government agencies monitoring dental diagnostic results from diagnostic device 110 or other such oral health diagnostic systems. A user operating workstation 170 is preferably presented with reports that includes information such as, but not limited to, patient identifier, oral health risk assessment, tooth number and surface, images of examined surfaces, x-ray of the examined tooth, ICDAS ranking, other oral screening ranking systems, dental diagnostic device data, diagnostic tests and other notations. The reports may contain visual images, x-ray images and information on the ongoing health of the tissue or material under observation. The information is stored by patient (with adequate privacy protection in place) or by population based upon geographic or other population based systems.

These separate bundles of information and/or data support unique data analysis for a variety of different stakeholders. For example, one can create a database relating to the patient that the patient and/or their oral health care provider could follow. It would be set up by date and tooth or for the entire dentition and contain the device information obtained from the processed scan data on a particular tooth along with a visual image of the surface and an assessment of risk for disease or status of disease on the particular hard or soft tissue under examination.

Figure 6:
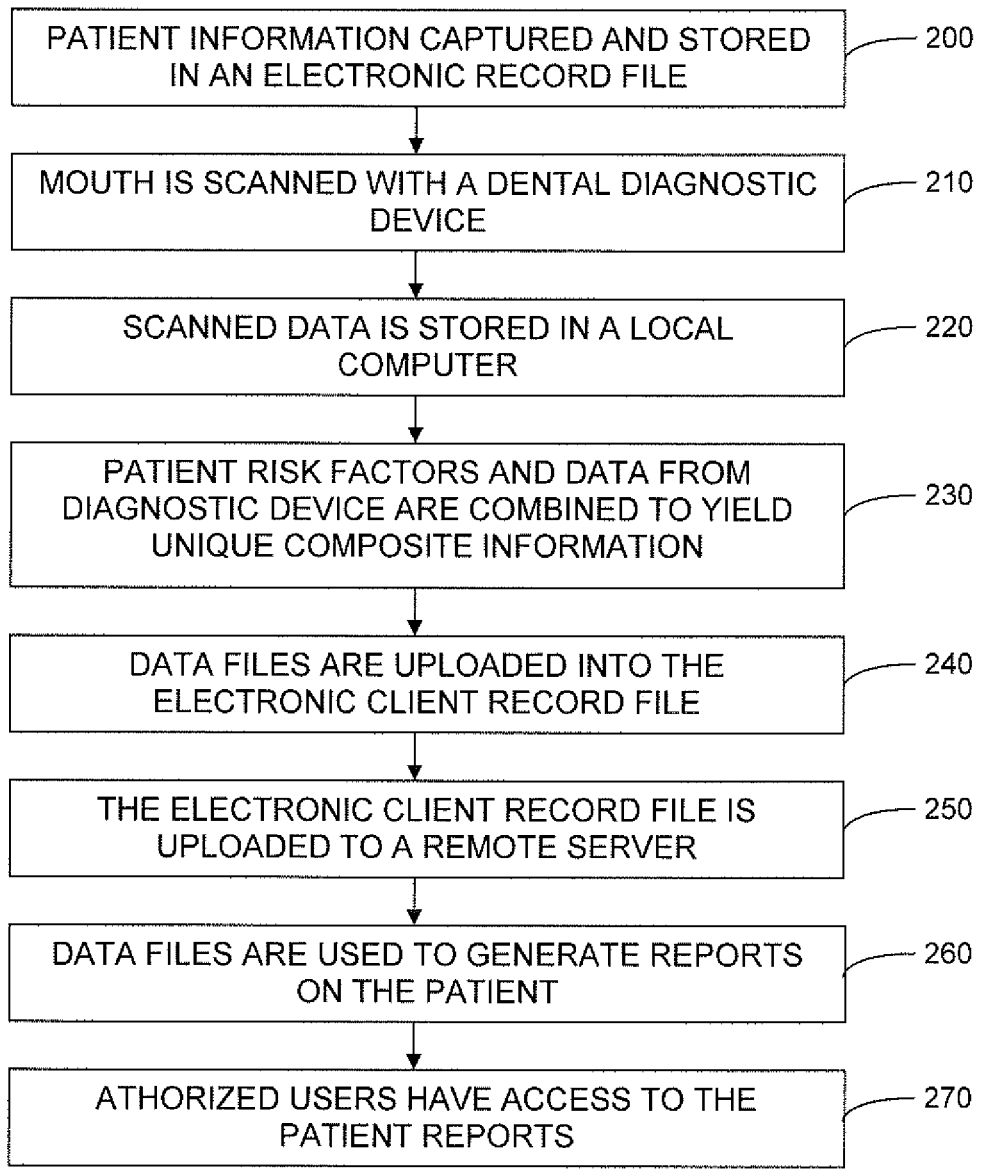
FIG. 6 provides a flow chart illustrating a preferred embodiment of the method according to the present invention.

Such a method of utilizing the system 100 is illustrated in the flow chart shown in FIG. 6. In step 200, patient information is inputted and stored electronically. This patient information preferably includes the patient risk factor data described in the preceding embodiments. The dental diagnostic device is then used in step 210 to scan the mouth of a patient and or the patient's dentition, thus generating diagnostic data. The diagnostic data is preferably stored locally in step 220, for example, in a local computer or in a memory of the detection device. In step 230, the diagnostic data and the patient risk factors are combined to provide a composite risk assessment, preferably, using the method shown in FIG. 1, where an integrated risk measure is obtained. The integrated risk measure, patient information, and preferably the diagnostic data and risk factor data is electronically uploaded in to the patient electronic record in step 240. Preferably, this uploaded file is sent to a remote server in step 250, where it is used to generate one or more reports in step 260 and made available for external access to authorized users in step 270.

In one embodiment, the oral health care provider can be provided with a report on their particular practice ranked by size of lesion and location of lesion or age of patient with respect to number of lesions. The information may be provided to public health and government agencies with data on a particular population based upon geographic location (for example, postal code), dental program (social assistance program), tooth, age and/or surface. The information may also be provided to pharmaceutical manufacturers with data on the disease rates in a community and design very simple clinical trials using tooth pastes and other remineralizing agents. The "other notations" section may contain information on therapies in progress and notes on overall oral hygiene, influence of diet or medications. The information may be provided to dental insurers and/or third party payors seeking information on dental caries in their particular employee group and also a visual image of the tooth and lesion in question. In a preferred embodiment, a numerical display is shown linked to a visual image, giving the third party carrier some confidence that a scan has been done (even if pathology is not visible on the x-ray or the image) and that therapy including remineralization or placement of a filling is required.

The dental diagnostic device preferably provides an accurate method for data capture and analysis and substantially removes the human element from this function. It may be done in individual dental offices, clinical settings or field trials. This data may then be combined with data from other devices to provide a broad based survey. High risk populations may be identified by analyzing data capture by geographic or epidemiologic identifiers.

In a preferred embodiment, the method includes comparing the diagnostic data against a norm or standard to measure mineral loss or changes in the tooth or root or areas around dental restorations. Based on this comparison, recommendations may be made by the oral health care provider for therapies based upon the information from this device or in combination with information from other devices or risk assessments, such as x-rays and the like. This comparative and/or time-dependent data is preferably uploaded from the dental device to a central computer for further study including epidemiologic analysis by population including age, location, tooth, site and or surface and therapy. The data is preferably conveyed to one or more work stations that may be used by various authorized stakeholders (patients, oral health care providers, pharmaceutical companies, benefit plan administrators and or government agencies).

The data may be conveyed to researchers and or third parties for analysis and the information may be loaded on a web based, internet based, electronic based or other type of information based portal where the patient can access both their own data, therapies tailored to their particular condition or situation and information on new techniques to treat, prevent or detect further changes in their oral health condition. The data may also be accessed for analysis by users interested in looking at population based health including oral diseases such as caries or periodontal disease or diseases of hard and soft tissues. The data may also be provided to individuals interested in clinical trials of various therapies to either detect disease or heal diseased tissue or slow down the progress of disease such diseases as caries, periodontal disease and other oral disease that affect hard and soft tissues.

Reports may be prepared based on the data for the patient looking at ongoing oral health trends for their particular situation. Reports may be prepared for the oral health care provider to include in a chart or information storage system for each patient. Reports may be prepared for the oral health care provider to use with the patient, third party payors, benefit plan administrators and government agencies for reporting and billing purposes.

Embodiments of the present invention are advantageous because they provide a system which includes a device to capture data on a particular oral health condition including caries periodontal disease or oral cancer. The system not only captures the information from the oral tissues using the device, but also captures data on the health history, social history, diagnostic tests relevant to the patient so that one can create a report that provides a measurement of the status of the particular oral tissue and the risks of developing further problems with this tissue. In addition the database and device can also be configured to capture longitudinal data on the patient so that one may develop long term information on the patient, groups of patients (population based statistics). In addition, one may employ the integrated system, health history and data base to monitor ongoing changes when various therapies are applied to this particular oral tissue.

The following examples are presented to enable those skilled in the art to understand and to practice the present invention. They should not be considered as a limitation on the scope of the invention, but merely as being illustrative and representative thereof.

EXAMPLE 1

Utility of PTR-LUM (Canary Dental Caries Detection System™)
Diagnostic Data

In a PTR or PTR-LUM system, such as The Canary Dental Caries Detection System™, a beam of energy (typically a laser) intensity-modulated at a certain frequency is focused onto the sample surface. The resulting periodic heat flow due to the absorbed optical energy in the material is a diffusive process, producing a periodic temperature rise (distribution) which is called a "thermal wave". This temperature distribution in turn causes a modulated thermal infrared (black-body or Planck radiation) emission which is used to monitor the material under examination. PTR has the ability to penetrate, and yield information about, an opaque medium well beyond the range of optical imaging. Specifically, the frequency dependence of the penetration depth of thermal waves makes it possible to perform depth profiling of materials.

In PTR applications involving turbid media, such as hard dental tissue, depth information is obtained following optical-to-thermal energy conversion and transport of the incident laser power in two distinct modes: conductively, from a near-surface distance controlled by the thermal diffusivity of enamel (50-500 μm) [Brown W S, Dewey W A, Jacobs H R: Thermal properties of teeth. J Dent Res 1970; 49: 752-754] and radiatively, through blackbody emissions from considerably deeper regions commensurate with the optical penetration of the diffusely scattered laser-induced optical field (several mm). For example, deeper subsurface lesions are possible by using a longer wavelength (830-nm) laser source than a 659-nm probe [Jeon, R. J., Han, C., Mandelis, A., Sanchez, V., Abrams, S. H., "Non-intrusive, Non-contacting Frequency-Domain Photothermal Radiometry and Luminescence Depth Profilometry of Carious and Artificial Sub-surface Lesions in Human Teeth," Journal of Biomedical Optics 2004, July-August, 9, #4, 809-819].

PTR measurements of artificially induced caries on human teeth have shown that the PTR amplitude increases gradually with increasing demineralization time and decreases after remineralisation. The PTR phase also shows gradual and consistent changes with demineralization and demineralization treatment. This behaviour has been attributed to the higher scatter of the diffuse photon field and to thermal-wave confinement in the form of standing waves in the treated region, accompanied by decreased thermophysical properties (thermal diffusivity and thermal conductivity).

Good correlation of PTR-LUM results with the mineral loss or the lesion depth measured with TMR results has indicated that PTR-LUM is capable of monitoring artificially created carious lesions, their evolution during demineralization, and the reversal of the lesions under the growth of a remineralized surface layer [Jeon R. J., Hellen A., Matvienko A., Mandelis A., Abrams S. H., Amaechi B. T., In vitro Detection and Quantification of Enamel and Root Caries Using Infrared Photothermal Radiometry and Modulated Luminescence. Journal of Biomedical Optics 13(3), 048803, 2008]. The PTR-LUM methodology for dental applications has been extensively studied. Literature reports include applications in depth profiling, early lesion evaluation, caries detection in smooth, occlusal, root and interproximal areas, and theoretical modeling.

One of the main advantages of PTR-LUM is the ability to perform depth profiling through scanning of the excitation source modulation frequency. By selecting a fixed modulation frequency, radiometric measurements at different depths in the enamel can be obtained. The first attempt to apply the depth profilometric capability of PTR-LUM toward the inspection of dental defects was reported by Mandelis et al. [Jeon, R. J., Mandelis, A., Abrams, S. H., "Depth profilometric case studies in caries diagnostics of human teeth using modulated laser radiometry and luminescence", Review of Scientific Instruments, 2003, January, Volume 74 #1, pages 380-383]. In these studies a laser of 488 nm was used as the excitation source. This work showed that the photothermal radiometric signals were anti-correlated with the luminescence signals, as a result of the nature of the two physical signal generation processes. While the PTR amplitude increased for carious lesions the LUM amplitude decreased. The LUM signal results were consistent with previous reports [R. Hibst et al.]. In addition, these studies showed that the radiometric amplitude exhibited much superior dynamic (2 orders of magnitude signal resolution) range to luminescence (a factor of 2 only) in distinguishing between intact and cracked sub-surface structures in the enamel. Furthermore, the radiometric signal (amplitude and phase) produced dental images with much better defect localization, delineation, and resolution than those obtained with modulated luminescence.

Further experimental studies [Jeon, R. J., Han, C., Mandelis, A., Sanchez, V., Abrams, S. H., "Non-intrusive, Non-contacting Frequency-Domain Photothermal Radiometry and Luminescence Depth Profilometry of Carious and Artificial Sub-surface Lesions in Human Teeth," Journal of Biomedical Optics 2004, July-August, 9, #4, 809-819] used excitation sources of 659 and 830 nm to assess the feasibility of PTR-LUM to detect deep lesions. PTR frequency scans over the surface of an occlusal fissure into demineralized enamel and dentin showed higher amplitude than those for healthy teeth, as well as a pronounced curvature in both the amplitude and phase signal channels. These can be excellent markers for the diagnosis of subsurface carious lesions. The results showed that PTR-LUM is able to detect artificial subsurface defects with sharp boundaries at depths greater than 5 mm. In addition PTR exhibited superior sensitivity to the presence of sharp boundaries, as well as to changes in natural demineralized regions of the tooth. These results suggested the possibility to detect carious lesions on both occlusal surfaces and the interproximal area of the tooth [Jeon et al.].

In experimental studies, it was found that PTR Amplitude had a very strong correlation with lesion size and shape. LUM phase provided limited information. PTR Phase provided an indication of operator movement if there was a strong shift in the phase number from the norm. If this occurred, the operator was instructed to re-measure the area.

In a preferred embodiment providing a single unified quantitative indication of oral health from a measurement at a given location, the data from each location is stored as four separate signals; PTR amplitude and phase and LUM amplitude and phase. A unified diagnostic measure is obtained according to the following weighting formula:

PTR Amplitude weighted at 45% of the total value
PTR Phase weighted at 15% of the total value
LUM Phase weighted at 10% of the total value
LUM Amplitude weighted at 30% of the total value The four readings are compared to the readings one finds from the healthy enamel surface and/or from a standardized piece of hydroxyapatite. The measured signal number is compared to healthy enamel surface as well. Preferably, results from the comparison step are provided on a fixed scale for each reading, for example, on a scale of 1 to 100 (the scales need not be equal for each reading type), indicating a severity of a condition. The four fixed-scale results are then weighted as described above, providing the operator a ranking or range (for example, on a scale from 1-100) indicating the health of the area examined. The utility of multiple readings in diagnostic assessment with a PTR and LUM detection device was illustrated in Jeon [Jeon et al., "Diagnosis of Pit and Fissure Caries Using Frequency-Domain Infrared Photothermal Radiometry and Modulated Laser Luminescence", Caries. Res. 38, 497-513, 2004], In another embodiment, the reading from a single frequency is combined in the following manner: (PTR amplitude×PTR Phase)/(LUM Amplitude×LUM Phase) to create one single reading. Error checking is done by combining the standard deviation from each reading into one number as follows:

LUM amplitude×LUM Phase×PTR Amplitude×PTR Phase. The ratio of single reading/combined standard deviation is examined and if the ratio increases dramatically this indicates an error in the reading and this is conveyed to the operator. The single reading is then conveyed to the operator along with its difference from the single reading derived from examining health enamel and healthy teeth.

EXAMPLE 2

Photothermal Radiometric and Luminescence System

Figure 7:
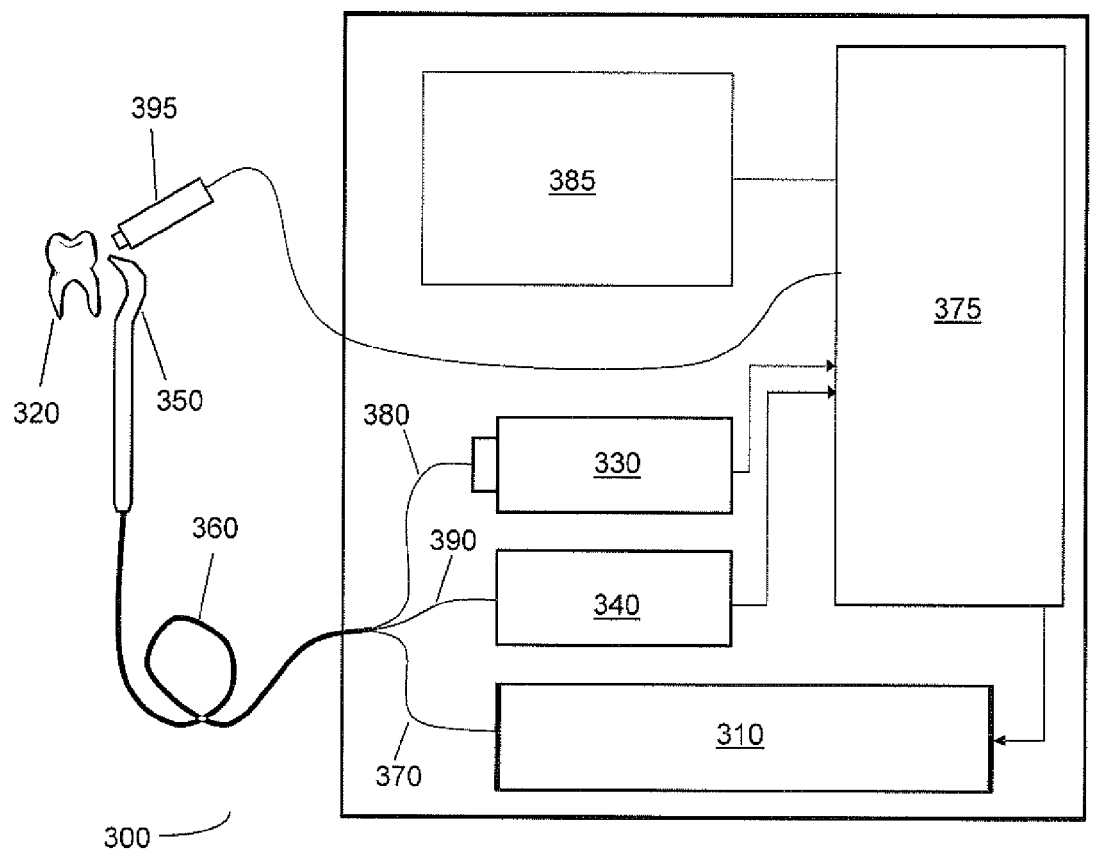
FIG. 7 is a schematic block diagram of an embodiment of the dental diagnostic device forming part of the dental data management system.

FIG. 7 illustrates non-limiting example of a diagnostic dental device according to a preferred embodiment of the invention involving a hybrid PTR-LUM device 300, shown with its main components. Details of the oral health detection device 300 are disclosed in United States Patent Publication No. US20070021670 published on Jan. 25, 2007, which is incorporated herein in its entirety by reference. U.S. Pat. No. 6,584,341 issued to Mandelis et al. entitled "Method and apparatus for detection of defects in teeth", which is incorporated herein in its entirety by reference, discloses a similar system. In a preferred embodiment, the system includes an optical imaging system, such as, but not limited to, a CCD camera for imaging capture of dental tissue. Other imaging devices may include an infra-red imaging device.

The PTR-LUM system 300 as disclosed in these two US patent publications is used for scanning and data capture of dental tissue. The device is designed for locating and monitoring small early carious lesions, areas of erosion and caries around restorations in a non-invasive fashion. The core technology in device is photothermal radiometry (PTR) and ac luminescence (LUM) as described in other the previously referenced United States patents/applications incorporated by reference. By using PTR and LUM and applying comparison to normal healthy enamel or other mineralized tissue, one can then assess the health of the tooth and monitor ongoing changes. The device can monitor ongoing demineralization (break down of the enamel crystal) and remineralization as well as erosion of the tooth surface or caries around dental restorations.

As shown in FIG. 7, the system includes a laser light source 310 for irradiating a portion of a dental surface 320 with an effective wavelength, in which modulated photothermal radiometric signals and modulated luminescence signals are responsively emitted from the dental surface. A first detector 330 detects the emitted modulated luminescence signals, and a second detector 340 detects the emitted modulated photothermal signals. The laser light is emitted from a hand held probe head 350, and a flexible optical fiber bundle 360 having a distal end connected is to the hand held probe head.

The optical fiber bundle includes a first optical fiber 370 having a proximal end in optical communication with the light source and a distal end terminated at the hand held probe head for transmitting light from the light source to a patient's dental tissue by a clinician handling the hand held probe head. The optical fiber bundle additionally includes a plurality of multi-mode optical fibers having distal ends 380 terminated at the hand held probe head and proximal ends optically coupled to the two detectors. A first pre-selected number of the multi-mode optical fibers 380 are near-infrared-transmitting optical fibers for transmitting the modulated luminescence signals to the first detector, and a second pre-selected number of the multi-mode optical fibers 390 are mid-infrared-transmitting optical fibers for transmitting the photothermal radiometry signals to the second detector.

Device 300 includes a demodulator for demodulating the emitted modulated photothermal signals into photothermal phase and amplitude components and the modulated luminescence signals into luminescence phase and amplitude signals. Device 300 further includes a computer processor for comparing the photothermal phase and amplitude signals to photothermal phase and amplitude signals of a reference sample and comparing the luminescence phase and amplitude signals to luminescence phase and amplitude signals of a reference sample to obtain differences, if any, between the portion of the dental tissue and the reference sample and correlating any differences with defects in the dental tissue. In FIG. 7, both the demodulator and the computer processor are shown generally as processing unit 375. A computer with touch screen 310, keyboard, and mouse input interface and included and a CCD camera 395 may be included for capturing images of the examined surface of the dental tissue of the patient.

Prior to initiating a scan, information relating to the identification of the patient and the oral tissue (teeth or gum or any other dental tissue and its location) are input through an input device 385 such as a touch screen. The resulting optical signal from sample 320 recorded using the device are collected by the hand piece 350 and optical fiber bundle 360 and sent to detectors 330 and 340. An image of the examined surface is obtained with the CCD camera 395 and sent to the processing unit 375. In an alternative embodiment, an imaging device (such as a CCD camera) may be integrated in the scanning hand piece 350. While a dental technician is operating device 300, the data is captured by scanning the tooth surfaces with an optical probe in hand piece 350.

Figure 8:
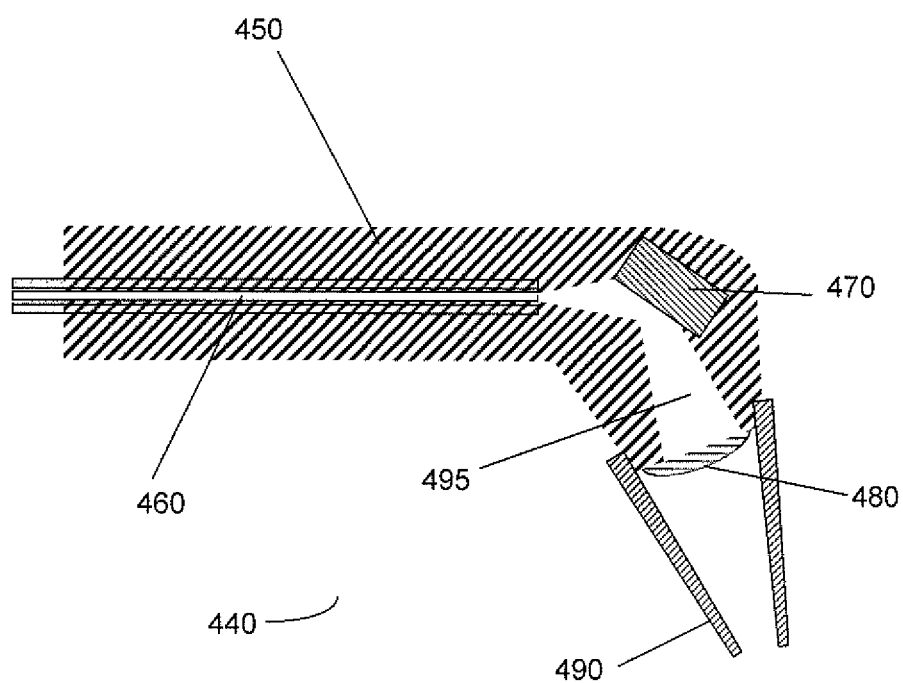
FIG. 8 is a schematic block diagram of an embodiment of the hand piece forming part of the dental diagnostic device and dental data management system.

An exemplary schematic of the internal optical configuration for the hand piece 350 is shown in FIG. 8. A housing 450 contains the optical fiber bundle 460, mirror 470, lens 480, and spacer 490. The optical fiber bundle 460 delivers the laser light (shown at 495) and collects the scanning results through mirror 470 and lens 480. While the system shown in FIG. 7 and its application have been described and illustrated within the context of an exemplary embodiment, it is to be understood that numerous embodiments of device system may be made without departing from the scope of the invention.

To obtain an output indicative of the oral health of a patient, the oral health detection device, such as the PTR-LUM device discussed above, analyzes the raw data captured from a patient and compares it to a normalized signal for that particular hard tissue. The norm could be either an internally generated function or the signal from a healthy section of hard tissue or a signal generated by hydroxyapatite or other mineralized tissue or commercially produced samples.

Scanning a tooth surface with the device can involve a single frequency, two or more selected frequencies or a frequency scan from 1 Hz to 1000 Hz. In a preferred embodiment, the device is scanned with the option of either 1 or 4 frequencies. The single frequency is used to examine a particular section of tooth surface such as a stained groove.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A computer implemented method of determining an oral health risk status of a patient, said method comprising the steps of:
   receiving diagnostic data pertaining to said patient from an oral health detection device;
   receiving risk factor data pertaining to said patient;
   processing said diagnostic data and said risk factor data on a processor to determine an oral health risk status of said patient, wherein said step of processing said diagnostic data and said risk factor data comprises:
   determining one or more diagnostic risk measures based on said diagnostic data, wherein at least one of said diagnostic risk measures is obtained by processing a measured diagnostic value and one or more previously measured diagnostic values for said patient, and relating a rate of change of said measured diagnostic value to a risk of developing a deterioration in oral health;
   determining one or more patient risk measures based on said risk factor data; and
   combining said diagnostic risk measures and said patient risk measures to obtain an integrated risk measure associated with said oral health risk status of said patient.

2. The method according to claim 1 further comprising the step of storing said integrated risk measure with a patient-specific identifier.

3. The method according to claim 1 further comprising the step of storing said integrated risk measure in a patient record.

4. The method according to claim 1 wherein said diagnostic risk measures and said patient risk measures are stored with said integrated risk measure.

5. The method according to claim 1 wherein said integrated risk measure relates to one or more teeth, wherein said integrated risk measure is recorded with additional information identifying said one or more teeth.

6. The method according to claim 1 wherein said device detects one or more conditions selected from the group consisting of demineralization of teeth, remineralization of teeth, presence of dental caries on enamel, presence of dental caries on root surfaces, erosion, defects in restorations, defects and caries along the margins of restorations, dental caries, cracks, periodontal disease, diseases of the hard and soft tissues, and oral cancer.

7. The method according to claim 1 wherein said device detects changes associated with the dental health of a tooth.

8. The method according to claim 7 wherein said changes comprise one of demineralization of the enamel surface, demineralization of the root surface, remineralization of the root surface, remineralization of the enamel surface, restoration in and on the tooth, restoration of surrounding tissue of a tooth, and a combination thereof.

9. The method according to claim 1 wherein said device measures a signal comprising one of fluorescence, luminescence, photo-thermal radiometry, and a combination thereof.

10. The method according to claim 9 wherein said device comprises a phase-sensitive detection system which detects the phase change associated with one or more of said fluorescence, luminescence, photo-thermal radiometry signals.

11. The method according to claim 1 wherein said diagnostic data comprises signals measured by said device and wherein said processor processes said signals and compares said signals to reference values to determine a severity of an oral health condition prior to said step of determining said diagnostic risk measures.

12. The method according to claim 11 wherein said step of determining a severity of an oral health condition comprises determining one of a number of dental caries, a severity of one or more dental caries, a number or demineralization areas, a severity of one or more demineralization areas, a number of white spots, a number of brown spots, a severity of one or more white spots, a severity of one or more brown spots, and a combination thereof.

13. The method according to claim 1 wherein said diagnostic data comprises a determination of a severity of an oral health conditions based on measurements performed by said device.

14. The method according to claim 13 wherein said diagnostic data comprises one of a number of dental caries, a severity of one or more dental caries, a number or demineralization areas, a severity of one or more demineralization areas, a number of white spots, a number of brown spots, a severity of one or more white spots, a severity of one or more brown spots and a combination thereof.

15. The method according to claim 14 wherein said severity of an oral defect is determined according to one of a standard ranking scale and a scale developed for the device.

16. The method according to claim 1 wherein said risk factors are patient-specific risk factors predictive of risk of developing a deterioration in oral health.

17. The method according to claim 16 wherein one or more of said risk factors are obtained from a patient questionnaire.

18. The method according to claim 16 wherein said risk factors comprise one or more of pathological risk factors, protective risk factors, historical risk factors, self-care risk factors, behavioral risk factors, and extrinsic risk factors.

19. The method according to claim 18 wherein one or more of said pathological risk factors are selected from the group consisting of a plaque index, quantity of existing tooth decay, size of existing tooth decay, distribution of existing tooth decay, presence of acidogenic bacteria, presence of pathologic bacteria, reduced salivary flow, bleeding of gums when brushed, bleeding of gums when flossed, number of decayed, missing teeth, filled teeth, crowding of the teeth, mal-alignment of the teeth, frequency of carbohydrate ingestion, and timing of carbohydrate ingestion.

20. The method according to claim 18 wherein one or more of said protective risk factors are selected from the group consisting of use of remineralization agents, an amount of salivary flow, the presence of salivary components comprising one or more of proteins, calcium, phosphate, fluoride, immunoglobins, and antibacterials in saliva.

21. The method according to claim 18 wherein one or more of said behavioral risk factors are selected from use of selected chewing gums and consumption of dairy products, and tendency to grind teeth.

22. The method according to claim 18 wherein one or more of said self-care risk factors are selected from the group consisting of frequency of tooth brushing, timing of oral health maintenance including one or more of brushing and flossing, frequency of tooth flossing, manual dexterity and ability to properly use various oral health aids properly including a tooth brush, use of a fluoridated toothpaste, use of other oral health home care aids, and use of selected mouth rinses.

23. The method according to claim 18 wherein one or more of said historical risk factors are selected from the group consisting of an integrity of a tooth surface, a status of oral tissues, a history of grinding teeth, exposed root surfaces, number of years living in a fluoridated community, and a number within a prescribed period of fillings, root canals, crowns, bridges, partial dentures, tooth extractions, oral and periodontal surgical procedures and implants.

24. The method according to claim 18 wherein one or more of said extrinsic risk factors are selected from the group consisting of diet, sufficiency of home care, access to oral care, gender, age, geographic location, socio-economic status and one or more demographic factors.

25. The method according to claim 1 wherein said step of processing said diagnostic data and said risk factor data further comprises:
comparing said diagnostic data to pre-determined risk-associated diagnostic values to obtain said diagnostic risk measure; and
comparing said risk factor data to pre-determined risk-associated risk factor values to obtain said patient risk measures.

26. The method according to claim 1 wherein said step of processing said diagnostic data and said risk factor data further comprises:
comparing said diagnostic data to pre-determined diagnostic values, each said pre-determined diagnostic value having associated therewith a risk score, wherein said diagnostic risk measures are said risk scores associated with the pre-determined diagnostic values closest to said diagnostic data;
comparing said risk factor data to pre-determined risk factor values, each said pre-determined risk factor value having associated therewith a risk score, wherein said patient risk measures are risk scores associated with the pre-determined risk factor values closest to said risk factor data.

27. The method according to claim 26 wherein said step of combining said risk measures to obtain an integrated risk measure associated with said oral health risk status of said patient comprises:
multiplying each said risk measure by a pre-determined weighing factor to obtain weighed risk measures;
combining said weighed risk measures to obtain said integrated risk measure.

28. The method according to claim 27 wherein prior to said step of multiplying each said risk measure by a pre-determined weighing factor, said risk measures are multiplied by a confidence factor relating to a value of said risk measure.

29. The method according to claim 27 further comprising normalizing said integrated risk measure to a pre-determined value.

30. The method according to claim 27 wherein said step of combining said weighed risk measures comprises adding said weighed risk measures.

31. The method according to claim 1 further comprising comparing said integrated risk measure to a set of ranges, each range having associated therewith a qualitative risk assessment, and selecting the qualitative risk assessment corresponding to said integrated risk measure.

32. The method according to claim 31, further comprising displaying said selected qualitative risk assessment in one of a graphical format and a report format.

33. The method according to claim 1 further comprising providing a treatment recommendation based on one or more of said diagnostic risk measures, said patient risk measures, and said integrated risk measure.

34. The method according to claim 1, further comprising the steps of:
repeating said steps for one or more additional patients and storing said integrated risk measures for each patient; and
performing one or more statistical analyses on said integrated risk measures.

35. The method according to claim 34 wherein said statistical analyses comprises one or more epidemiological analyses of said integrated risk measures, said epidemiological analysis comprising an analysis according to one of age, location, tooth, site, tooth surface, therapy, groups of teeth, an entire dentition and a combination thereof.

36. The method according to claim 1 further comprising providing said integrated risk measure to any one or combination of pharmaceutical manufacturers, oral therapeutics manufacturer, oral therapeutics distributor, public health agencies, government agencies, oral health professionals, research scientists, academic institutions, insurers, and third party payors.

37. The method according to claim 1 wherein said steps are performed at a location that is local relative to said detection device.

38. The method according to claim 37 wherein one or more of said diagnostic data and said risk factor data is provided to said processor through a network.

39. The method according to claim 1 wherein said steps are performed at a location that is remote relative to said detection device.

40. The method according to claim 39 wherein one or more of said diagnostic data and said risk factor data is provided to said processor through a remote network.

41. The method according to claim 1 further comprising storing said integrated risk measure on one of a remote server, a cloud computing environment, and a combination thereof.

42. A computer implemented method of obtaining data relating to a clinical trial for an oral product, therapy or treatment, said method comprising the steps of:
a) obtaining diagnostic data pertaining to a plurality of patients in said clinical trial from an oral detection device;
b) obtaining risk factor data pertaining to each patient of said plurality of patients;
c) processing said diagnostic data and said risk factor data on a processor to determine an oral health risk status of said each patient, wherein said step of processing said diagnostic data and said risk factor data comprises:
determining one or more diagnostic risk measures based on said diagnostic data, wherein at least one of said diagnostic risk measures is obtained by processing a measured diagnostic value and one or more previously measured diagnostic values for said each patient, and relating a rate of change of said measured diagnostic value to a risk of developing a deterioration in oral health;
determining one or more patient risk measures based on said risk factor data; and
combining said diagnostic risk measures and said patient risk measures to obtain an integrated risk measure associated with said oral health risk status of said each patient; and
d) after administration one a product, therapy and/or oral treatment to said patients, performing steps a)-c) to obtain post-treatment integrated risk measures associated with said oral health risk status of each patient.

43. A computer implemented method of determining an oral health risk assessment for a patient population, said method comprising the steps of:
obtaining diagnostic data pertaining to each patient in said patient population with an oral health detection device;
obtaining risk factor data pertaining to each patient;
processing said diagnostic data and said risk factor data on a processor to determine an oral health risk status of said each patient, wherein said step of processing said diagnostic data and said risk factor data comprises:
determining one or more diagnostic risk measures based on said diagnostic data, wherein at least one of said diagnostic risk measures is obtained by processing a measured diagnostic value and one or more previously measured diagnostic values for said each patient and relating a rate of change of said measured diagnostic value to a risk of developing a deterioration in oral health;
determining one or more patient risk measures based on said risk factor data; and
combining said diagnostic risk measures and said patient risk measures to obtain an integrated risk measure associated with said oral health risk status of said each patient.

44. The method according to claim 43 further comprising providing said integrated risk measure of said each patient to any one or combination of pharmaceutical manufacturers, oral therapeutics manufacturer, oral therapeutics distributor, public health agencies, government agencies, oral health professionals, research scientists, academic institutions, health care insurance companies, and third party payers.

45. A system for determining an oral health risk status of a patient, said system comprising:
a data interface for receiving diagnostic data from an oral detection device and risk factor data, wherein said diagnostic data and said risk factor data pertains to said patient;
a processor for processing said diagnostic data and said risk factor data to determine an oral health risk status of said patient, said processor programmed with computer-readable instructions to:
receive diagnostic data pertaining to said patient from an oral health detection device;
receive risk factor data pertaining to said patient;
determine one or more diagnostic risk measures based on said diagnostic data, wherein at least one of said diagnostic risk measures is obtained by processing a measured diagnostic value and one or more previously measured diagnostic values for said patient, and relating a rate of change of said measured diagnostic value to risk of developing a deterioration in oral health;
determine one or more patient risk measures based on said risk factor data; and
combine said diagnostic risk measures and said patient risk measures to obtain an integrated risk measure associated with said oral health risk status of said patient; and
an output means for one of displaying, recording, and exporting said integrated risk measure.

46. The system according to claim 45 wherein said output means comprises a local memory for storing said integrated risk measure.

47. The system according to claim 45 wherein said output means comprises a display device for displaying said integrated risk measure.

48. The system according to claim 45 wherein said output means comprises an additional interface for providing said integrated risk measure to one of an external computer, server, memory, and a combination thereof.

49. The system according to claim 48 wherein said additional interface is configured to convey said integrated risk measure to one or more remote work stations.

50. The system according to claim 45 further comprising said oral detection device.

51. The system according to claim 45 further comprising a data entry means for providing said risk factor data.

52. The system according to claim 45 wherein said processor is programmed with computer-readable instructions to:

compare said diagnostic data to pre-determined risk-associated diagnostic values to obtain said diagnostic risk measure; and compare said risk factor data to pre-determined risk-associated risk factor values to obtain said patient risk measure.

53. The system according to claim 45 wherein said processor is programmed with computer-readable instructions to:

compare said diagnostic data to pre-determined diagnostic values, each said pre-determined diagnostic value having associated therewith a risk score, wherein said diagnostic risk measure is said risk score associated with the pre-determined diagnostic value closest to said diagnostic data;

compare said risk factor data to pre-determined risk factor values, each said pre-determined risk factor value having associated therewith a risk score, wherein said patient risk measures are risk scores associated with the pre-determined risk factor values closest to said risk factor data.

54. The method according to claim 1 wherein said diagnostic data further comprises one or more images of an examined tooth surface.

55. The method according to claim 32 wherein said one of a graphical format and a report format comprises one or more images of an examined tooth surface.

* * * * *